(12) United States Patent
Binmoeller

(10) Patent No.: US 7,261,725 B2
(45) Date of Patent: Aug. 28, 2007

(54) ENDOSCOPIC DEVICE WITH INDEPENDENTLY ACTUATED LEGS

(76) Inventor: Kenneth F. Binmoeller, P.O. Box 5000, PMB 148, Rancho Santa Fe, CA (US) 92067

( * ) Notice: Subject to any disclaimer, the term of this patent is extended or adjusted under 35 U.S.C. 154(b) by 410 days.

(21) Appl. No.: 11/034,103

(22) Filed: Jan. 13, 2005

(65) Prior Publication Data

US 2006/0155310 A1 Jul. 13, 2006

(51) Int. Cl.
*A61B 17/08* (2006.01)
*A61B 17/10* (2006.01)

(52) U.S. Cl. ............... 606/151; 606/139; 606/205; 600/104; 433/159

(58) Field of Classification Search ........... 606/139, 606/142, 150–153, 156, 167, 170, 185, 128, 606/45–52, 110, 113, 127, 205–211; 600/101, 600/104, 106, 118, 136–139, 149, 153; 604/93.01; 29/243.521; 294/3, 8.5, 11, 119; 433/159
See application file for complete search history.

(56) References Cited

U.S. PATENT DOCUMENTS

| 6,520,908 | B1 | 2/2003 | Ikeda et al. | |
|---|---|---|---|---|
| 6,614,595 | B2 | 9/2003 | Igarashi | |
| 6,638,213 | B2 | 10/2003 | Ogura et al. | |
| 2004/0092962 | A1* | 5/2004 | Thornton et al. | 606/139 |
| 2005/0070926 | A1* | 3/2005 | Ortiz | 606/142 |
| 2005/0096673 | A1* | 5/2005 | Stack et al. | 606/151 |

* cited by examiner

*Primary Examiner*—Glenn K. Dawson
*Assistant Examiner*—Amanda Adams
(74) *Attorney, Agent, or Firm*—Scott M. Evans

(57) ABSTRACT

The present invention relates to endoscopic clips with multiple independently-controlled legs. The present invention also relates to a method for using a clip with multiple independently actuated legs. The clips and methods of the present invention may be used, for example and without limitation, for repairing tears and other defects endoscopically.

32 Claims, 10 Drawing Sheets

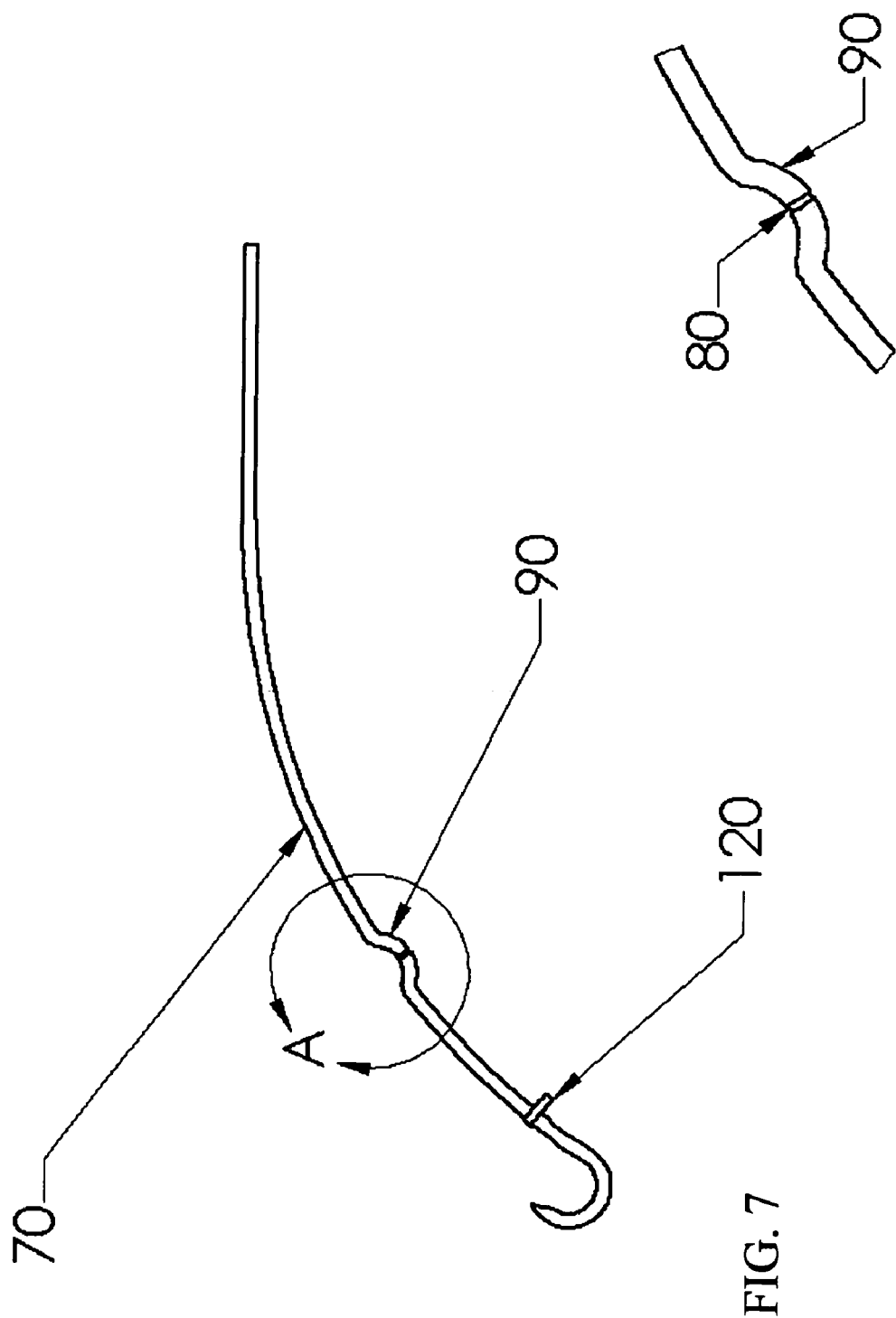

ENDOSCOPIC DEVICE WITH INDEPENDENTLY ACTUATED LEGS

FIELD OF THE INVENTION

The present invention relates to endoscopic clips with legs that may be advanced and controlled independently of each other, as well as methods of using the clips. The clips and methods of the present invention may be used, for example, to repair or suture tears or other defects endoscopically or in other environments where access is limited to a small incision or opening. The device and methods also may be used for approximation and fixation of tissue or other material.

BACKGROUND OF THE INVENTION

Less invasive surgical procedures can reduce patient trauma, and as a result, may reduce the length of hospital stays, as well as hospital and medical costs. Endoscopic surgery recently has provided a significant opportunity to reduce the invasiveness of numerous surgical procedures. This type of surgery involves the use of an endoscope, an instrument that permits the visual inspection and magnification of cavities within the body. Endoscopes may be flexible, semiflexible, or rigid. An endoscope may be inserted through a small surgical incision to view organ structures in a body cavity or through a natural orifice such as the mouth, anus, bladder, and vagina to view lumen-containing organs in the gastrointestinal, respiratory, and genital and urinary tracts. Endoscopes have channels for irrigation, suction, and the insertion of accessory instruments when a surgical procedure is performed During a surgical procedure, surgeons often are required to repair or reconstruct a tear or defect or otherwise approximate or fixate tissue or other material by suturing. However, the ability to suture through an endoscope technically is limited. In response to this problem, surgeons have sought alternatives to conventional suturing techniques that are more appropriate for use through an endoscope. Among these alternatives include the use of endoscopic clips.

While the use of endoscopic clips has alleviated some problems associated with suturing through the end of an endoscope, there is still room for improvement in their design and use. For instance, as presently used, the "legs" of clips are joined at their proximal ends. This configuration requires the distal ends of the legs to have a fixed distance and relationship between them. These fixed relationships limit a surgeon's ability to position the clip appropriately in relation to a particular tear or defect or other area in need of treatment. For instance, these clips may not be able to address a tear or defect with certain curves or angles and may not be able to span the width of a larger tear or defect. Further, because the proximal ends of the legs are joined, a surgeon may not be able to adjust the positioning of one leg of the clip without affecting the positioning of the second leg. Positioning also may be limited because the clip may not be properly oriented when it is placed within the actuating jaws of the cannula, or the clip may slip out of alignment during application. Finally, the legs of presently-used clips must be actuated and anchored at the same time. If unequal pressure is applied to the legs during anchoring, scissoring of the legs may occur and further tissue damage may result.

SUMMARY OF THE INVENTION

The present invention solves many of the described problems associated with presently-used endoscopic clips. The present invention may solve these problems by providing an endoscopic clip with independently-controlled legs that are not joined at their proximal ends.

One embodiment of the present invention may be a device comprising an outer tube with a proximal end and a distal end; a pusher tube assembly comprising an inner tube with a proximal end and a distal end and an end cap secured to the distal end of the inner tube; a clamp collar within the distal end of the inner tube; legs, each having a proximal end and a distal end; a retainer located proximally to the clamp collar with slots that allow passage of the legs; and an actuating member connected to the proximal end of the legs. Each leg may have an outwardly-oriented tab. The distal ends of the legs may be located, before deployment, at the distal end of the inner tube but proximal to the clamp collar. The legs, actuating members and retainer may reside within the inner tube. The outer tube and the inner tube may be connected to a proximal handle that may actuate each leg independently through a separate control cable connected to the proximal end of each leg's actuating member. The distal end of the legs may comprise a hook having a back end. The leg or hook may have a barb. The legs or hook may have a sharpened end. This sharpened end may be protected when the legs have been extended from the device and are in a closed and locked position. The back end of the hook may be angled outwardly within the inner tube.

In one embodiment of the present invention the actuating members may be guide blocks. In addition, the proximal handle may rotate the inner tube independently of the outer tube. The handle also may control the inner tube and the actuating members of the legs. The clamp collar may have slots that allow passage of the legs. The device may comprise two, three, four, or more legs.

The device may be used to interlock the legs of the present invention and the interlocked legs may be released. The legs may have a weakened portion that can break and separate the legs from the device once the legs are extended from the endoscopic device and in a closed and locked position.

The inner tube may be a coiled stainless steel tube. The legs may be made from a spring material. The outer and/or inner tubes may have a coil toward their distal ends. The control cables may, in one specific embodiment, have a diameter of about 0.50 mm. The outer tube may, in one specific embodiment, have an outer diameter of about 2.5 mm. The outer tube may, in one specific embodiment, have an inner diameter of about 2.0 mm. The inner tube may, in one specific embodiment, have an inner diameter of about 1.5 mm. The legs may, in one specific embodiment, be formed with a wire with a diameter of about 0.25 mm prior to hardening.

The present invention further comprises a method of using the above described device for endoscopically joining target material. This method comprises extending a first leg from said inner tube; engaging target material with said distal end of said first leg; extending a second leg from said inner tube; engaging target material with said distal end of said second leg; drawing said legs together into an interlocked position; and releasing said legs in said interlocked position from said device. The method further comprises repeating said extending and said engaging with additional legs as needed. Extending and engaging of the legs may be accomplished by sliding the actuating members connected to the proximal ends of the legs. The engaging step may further be accomplished by hooking and/or anchoring. The drawing step may be accomplished by sliding the inner tube over the extended and engaged legs. While the extension and engagement of the legs has been described as occurring sequentially, the extension and engagement of the legs also may occur simultaneously. The releasing step may comprise applying a force to the legs through the actuating members that may break the legs at the weakened portion of the legs.

The target material to be joined by the method may include, for example and without limitation, tissue, tissue surrounding a tear, tissue on alternate sides of a tear and/or a tissue defect. The method may be used, for example and without limitation, to repair a tissue defect, repair a tissue tear, anchor tissue or approximate or fixate tissue or other material.

BRIEF DESCRIPTION OF THE DRAWINGS

FIG. 7 is a detail plan view of an exemplary leg.

FIG. 8 is a detail of the weakened portion of an exemplary leg.

DETAILED DESCRIPTION OF PARTICULAR EMBODIMENTS

Figure 1:
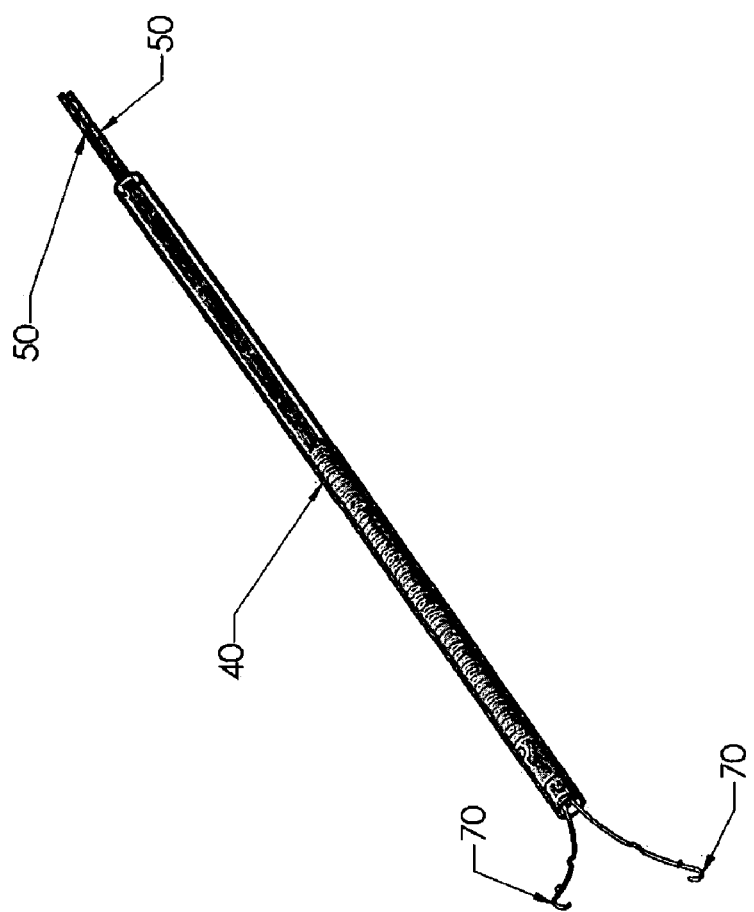
FIG. 1 is an isometric view of the distal end of one specific embodiment of the present invention with two legs of the clip advanced.

It is to be understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a leg" or "a clip" is a reference to one or more legs or clips and includes equivalents thereof known to those skilled in the art.

Unless defined otherwise, all technical and scientific terms used herein have the same meanings as commonly understood by one of ordinary skill in the art to which this invention belongs. Specific methods, devices, and materials are described, although any methods and materials similar or equivalent to those described herein can be used in the practice or testing of the present invention.

The term "patient," as used herein, comprises any and all organisms and includes the term "subject." "Patient" may refer to a human or any other animal.

In the following description it should be noted that directional terms such as "distal" and "proximal" are used relative to each other and do not refer to positions or orientations relative to an external frame of reference. Also, "locked" and "interlocked" are coextensive in meaning.

The terms "endoscope" or "endoscopic" refer not only to conventional endoscopes and endoscopic procedures, but also to any rigid, semi-rigid, or flexible optical instrument for use in visual examinations where access is limited to a small incision or opening. Generally, such examinations will occur in the human body, however, the use of the terms is not so restricted. References to endoscopes and endoscopic procedures must be understood also to encompass procedures in all organisms, living or dead, as well as, the examination of inanimate objects through small openings. Endoscopes and endoscopic procedures also must be understood to include laparoscopic devices and laproscopic procedures. The term "endoscope" also includes echo-endoscopes, which may include an ultrasound transducer at, for example, the tip of the device.

The term "material" refers to the substrate that is engaged by the legs of the present invention. Often the material engaged will be tissue within a body; however use of the term is not so limited.

The terms "join or joining" include repair of a tear or defect in any material that may be engaged, hooked or pierced by the legs of the present invention and specifically includes closure of tears or other defects and apposition of tissue or other material, analogous to that caused by conventional suturing or stapling, in endoscopic procedures, as well as grafting healthy tissue or other material onto areas of defective tissue or other material. The term also includes traversing and/or anchoring one or more layers of tissue that can be accessed endoscopically, such as, for example and without limitation, the wall of a hollow or solid organ, duct, vessel or soft tissue structure.

FIG. 1 through FIG. 11 depict exemplary devices and methods of the present invention. These devices and methods are depicted and described herein in order to better explain the invention. It will be understood that the devices and methods shown are representative only, and that devices of other configurations, sizes and styles are within the scope of this invention.

Referring to the Figures, FIG. 1 depicts an isometric view of the distal end of the device of the present invention with two legs 70 advanced. The legs 70 are shown protruding from the distal end of the outer tube 40. In the embodiment shown in FIG. 1, the legs 70 have hooks on their distal ends. In another embodiment of the present invention, the legs 70 may include hooks on their distal ends as well as a barbed anchoring member on the distal portion or tip of the leg. In another embodiment of the present invention, the legs 70 may include hooks on their distal portion or end as well as multiple barbed anchoring members. In another embodiment of the present invention, the legs 70 may lack the hook on their distal ends and instead have one or more barbed anchoring member on the distal tips of the legs. The legs 70 within a given device may have any combination of the hook and barbed anchoring member configurations described above. For instance, in one embodiment, all legs 70 may have the same configuration. In another embodiment, the legs 70 within a device may have different configurations.

In addition to the legs 70 of the device, FIG. 1 depicts two control cables 50 extending from the proximal end of the outer tube 40. The outer tube 40 may extend the full length of the device. The control cables 50 may be connected or connectable, at their proximal end, to a control in a hand piece (not shown). The outer tube 40 also may be connected or connectable to a hand piece on its proximal end.

Figure 2:
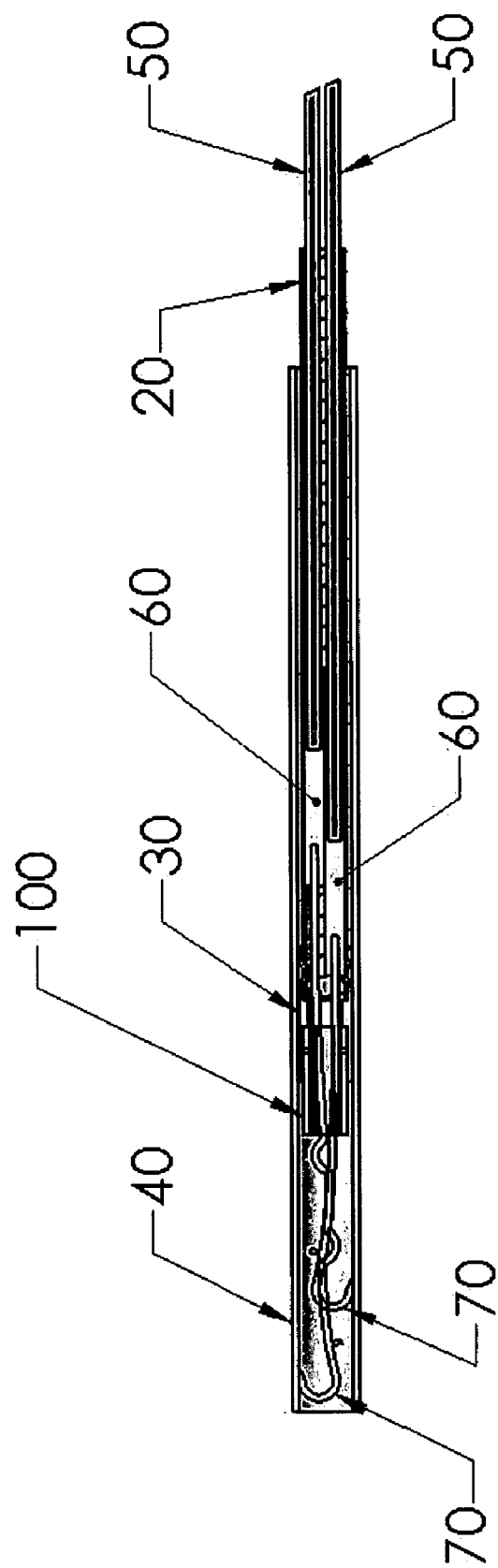
FIG. 2 is a longitudinal section view of the distal end of one specific embodiment of the present invention.

FIG. 2 is a longitudinal section view of a specific embodiment of the present invention. This view shows the control cables 50 connected to actuating members (guide blocks 60 in this Figure) that may be attached to the proximal ends of the legs 70 of the present invention, all within an inner tube 20 located within the outer tube 40. The inner tube 20 also has an end fitting 30 connected to its distal end that contacts the proximal end of the clamp collar 100. The inner tube 20 and end fitting 30 together form a pusher tube assembly (labeled as 10 in FIG. 5) that may advance the clamp collar 100 during deployment of the clip. In this configuration, the device may be fed through the working channel of an endoscope. The control cables 50 can transmit axial tension or compression to the guide blocks 60 in part due to support provided by the inner tube 20.

Figure 3:
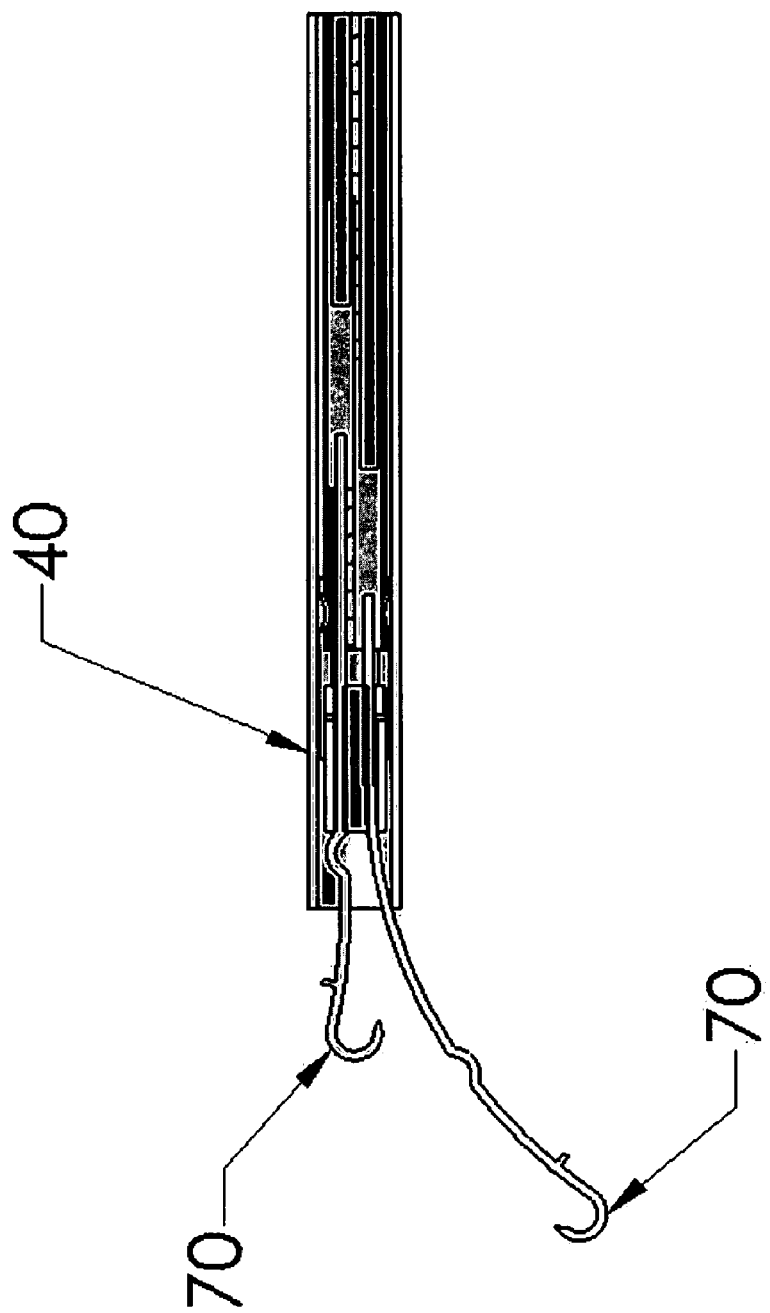
FIG. 3 is a longitudinal section view of the distal end of one specific embodiment of the present invention with one leg fully advanced and a second leg partially advanced.

FIG. 3 is a longitudinal section view of a specific embodiment of the device of the present invention. One leg 70 is depicted as fully advanced while a second leg 70 is depicted as partially advanced. FIG. 3 also shows the outer tube 40. While the embodiment depicted in this Figure depicts two legs 70, the device of the present invention is not limited to this embodiment. In another embodiment of the present invention the device may have two or more legs 70. In another embodiment, the device of the present invention may have three or more legs 70. In another embodiment, the device of the present invention may have four or more legs 70. In one embodiment of the present invention, all legs 70 may be located at the distal end of the device. In this embodiment, the guide blocks 60 may be half cylinders if there are two legs 70, third cylinders if there are three legs 70, quarter cylinders if there are four legs 70 and so forth. It is contemplated that each portion of the guide block 60 may have a control cable 50 attached to its proximal end. In another embodiment of the present invention, the legs 70 may be grouped into pairs of two, with the first pair located most distally, the second pair proximal to the guide blocks 60 of the first pair, the third pair proximal to the guide blocks 60 of the second pair and so forth. In this embodiment, each leg 70 of a pair may have a half cylinder guide block and the control cables 50 may be configured to travel along the outer circumference of the inner tube 20 to allow the successive pairs of legs 70.

When two legs 70 are included in an embodiment of the present invention or legs 70 are included as pairs, the guide blocks 60 may be half cylinders that may slide axially relative to the longitudinal axis of the device. The guide blocks 60 may have flat sides that may face each other within the inner tube 20. The length of the guide blocks 60 may be set so that the maximum relative displacement of the guide blocks 60 is less than the length of the guide blocks 60 themselves. In this configuration, the guide blocks 60 may remain mated along their faces.

Figure 4:
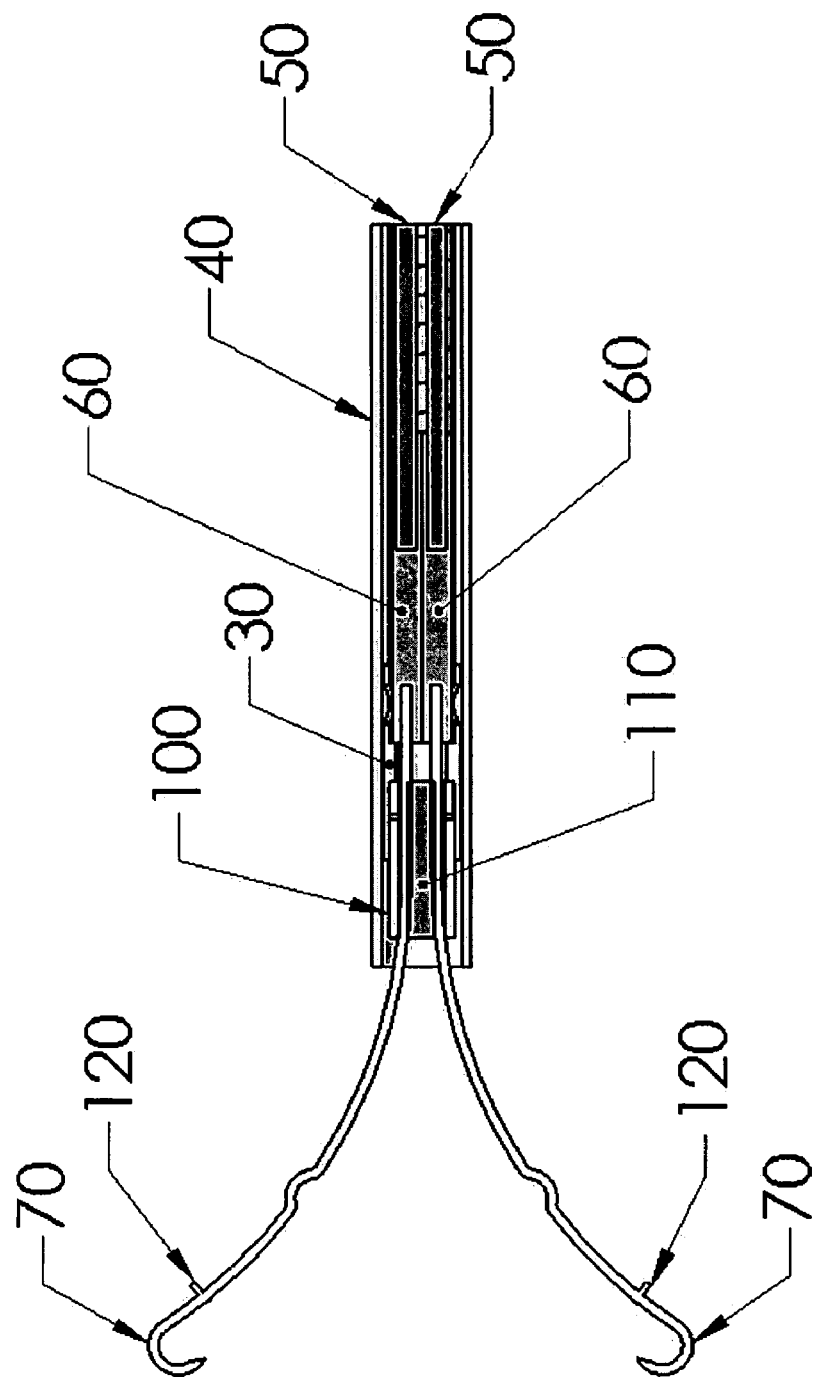
FIG. 4 is a longitudinal section view of one specific embodiment of the present invention with two legs fully advanced.

FIG. 4 depicts two legs 70 fully advanced and in an unlocked configuration. FIG. 4 also shows guide blocks 60 attached to the proximal ends of the legs 70, a retainer 110 that may be an elastomeric part of cylindrical shape with grooves that run its full length, and the clamp collar 100, which may be a tubular ring with slots that nests in the distal end of the device. The slots of the clamp collar 100 allow passage of the legs 70 during clip deployment. FIG. 4 also shows tabs 120 that may be found on the legs 70 of the present invention. Once the legs 70 have been advanced and engaged, the clamp collar 100 of the present invention may be advanced by the end cap 30 until the clamp collar 100 contacts these tabs 120. FIG. 4 also depicts the outer tube 40 and the control cables 50.

Figure 5:
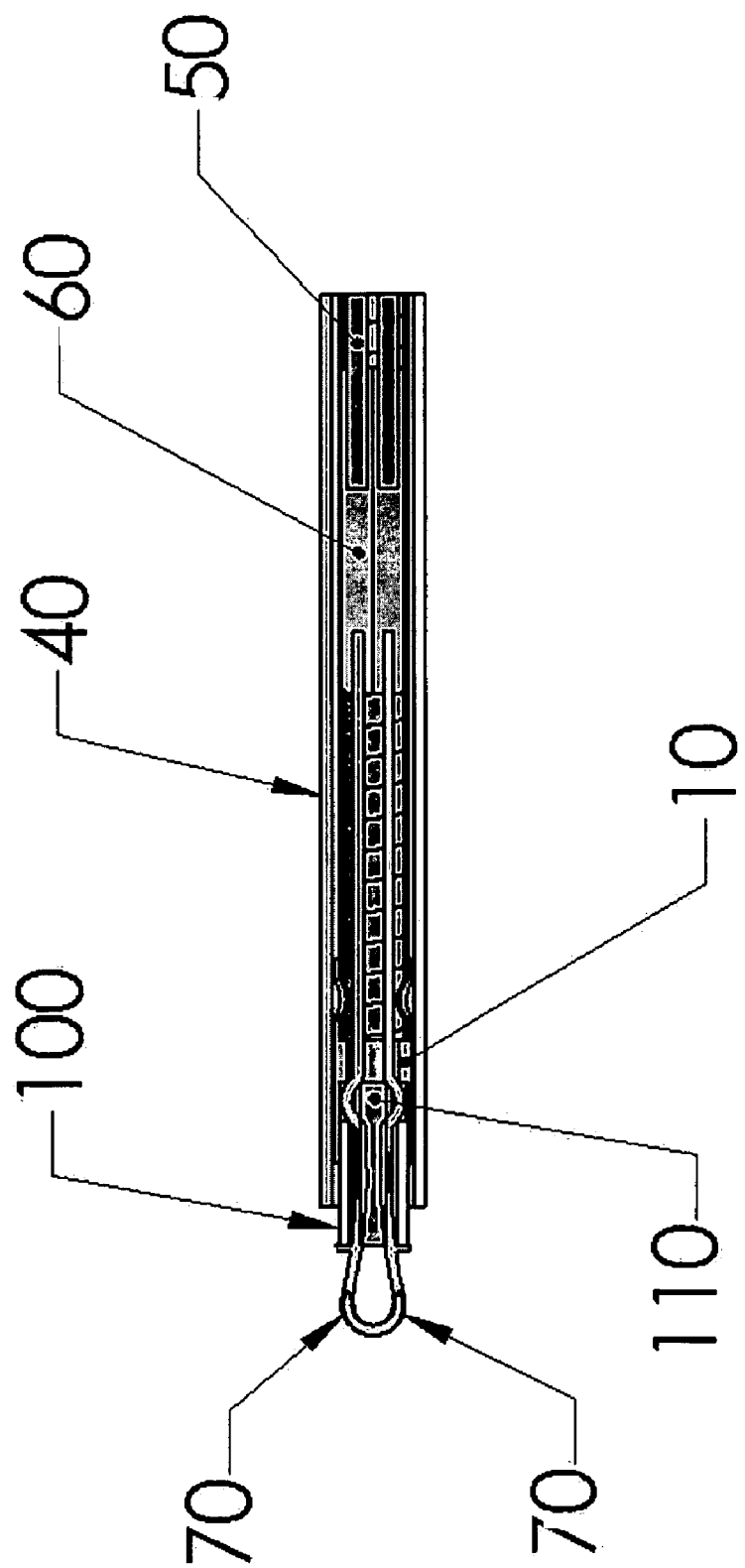
FIG. 5 is a longitudinal section view of the distal end of one specific embodiment of the present invention with the clamp collar advanced.

FIG. 5 is a longitudinal section view of one specific embodiment of the device of the present invention. In this Figure, two legs 70 have been advanced, and the clamp collar 100 also has been advanced to bring the legs into a locked position. The pusher tube assembly 10 (comprised of the inner tube 20 and end cap 30) pushes the clamp collar 100 toward the distal ends of the legs 70. Advancement of the clamp collar 100 may bring the legs 70 together into an interlocked position as shown in FIG. 5. If the legs 70 have been positioned properly, once pulled into the locked position by the clamp collar 100, they generally, for example, will have pulled the sides of a tear or defect together. FIG. 5 also depicts the outer tube 40, control cables 50, guide blocks 60 and the retainer 110.

Figure 6:
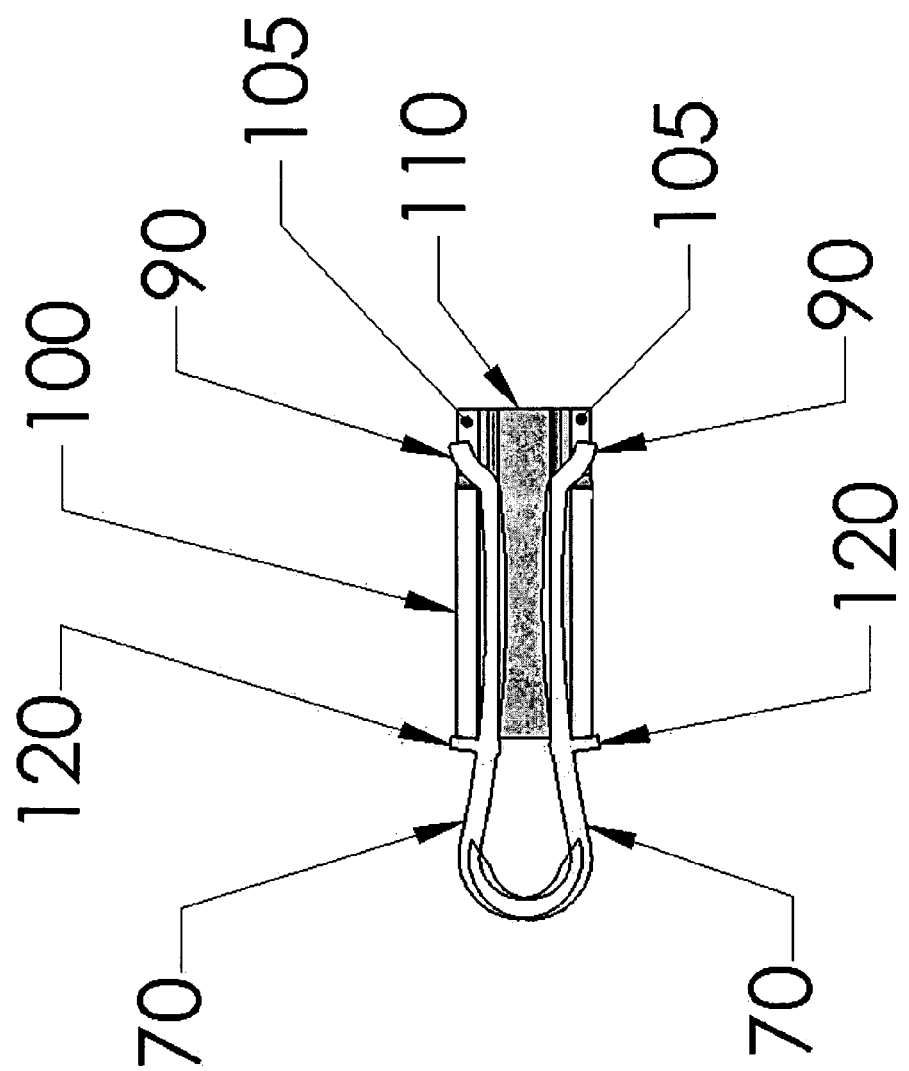
FIG. 6 is a longitudinal section view of an actuated clip after separation from the endoscopic device.

FIG. 6 is a close-up, longitudinal section view of a clip in its locked position. This Figure depicts the legs 70 of the clip after they have been drawn together by advancement of the clamp collar 100 to the tabs 120 on the legs 70. This Figure also depicts the slots 105 of the clamp collar 100 that accept the curved area 90 of the legs 70 as well as the retainer 110.

FIG. 7 is a detailed plan view of an exemplary leg 70 of the present invention. The leg 70, in this example, includes a hook on its distal end, a tab 120 and a curved area of the leg 90. In one embodiment, the curved area 90 of the leg 70 may contain a weakened zone 80. Stress within the curved area 90 of the weakened zone 80 may be intensified by bending moments produced by eccentric loading in the curved area 90 of the leg 70. FIG. 8 depicts weakened zone 80 in greater detail.

Figure 9:
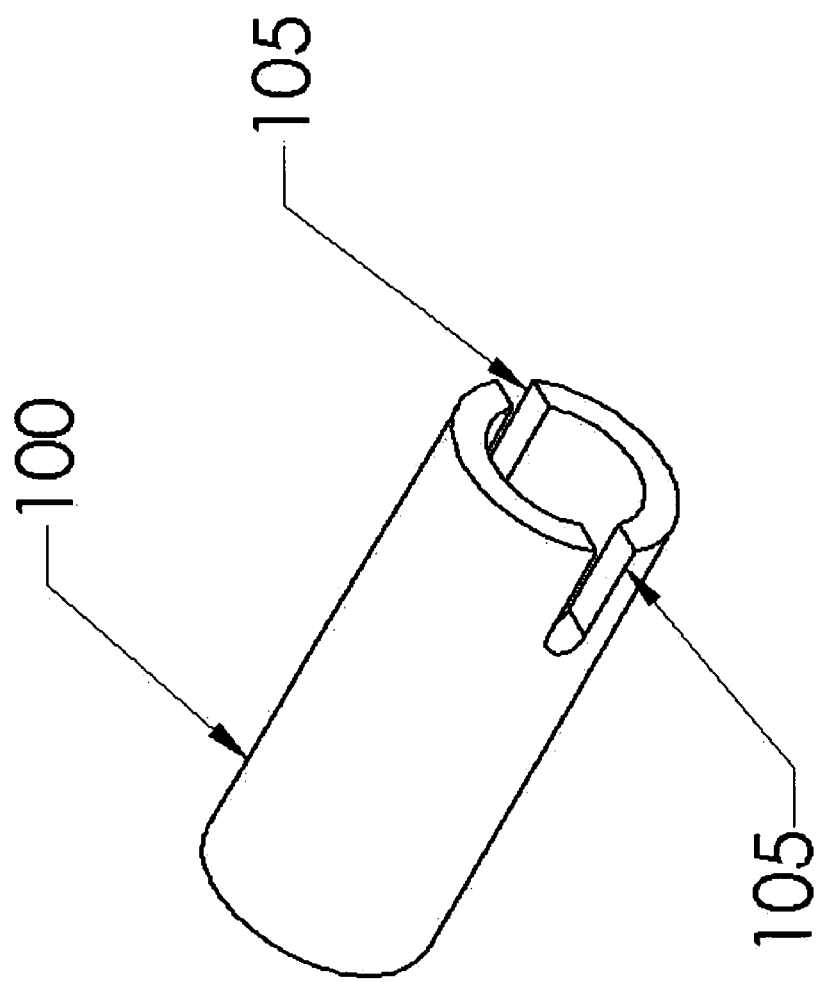
FIG. 9 is a detail isometric view of an exemplary clamp collar.

FIG. 9 is a detailed isometric view of an exemplary clamp collar 100 with slots 105 that allow passage of the legs 70 of the present invention.

Figure 10:
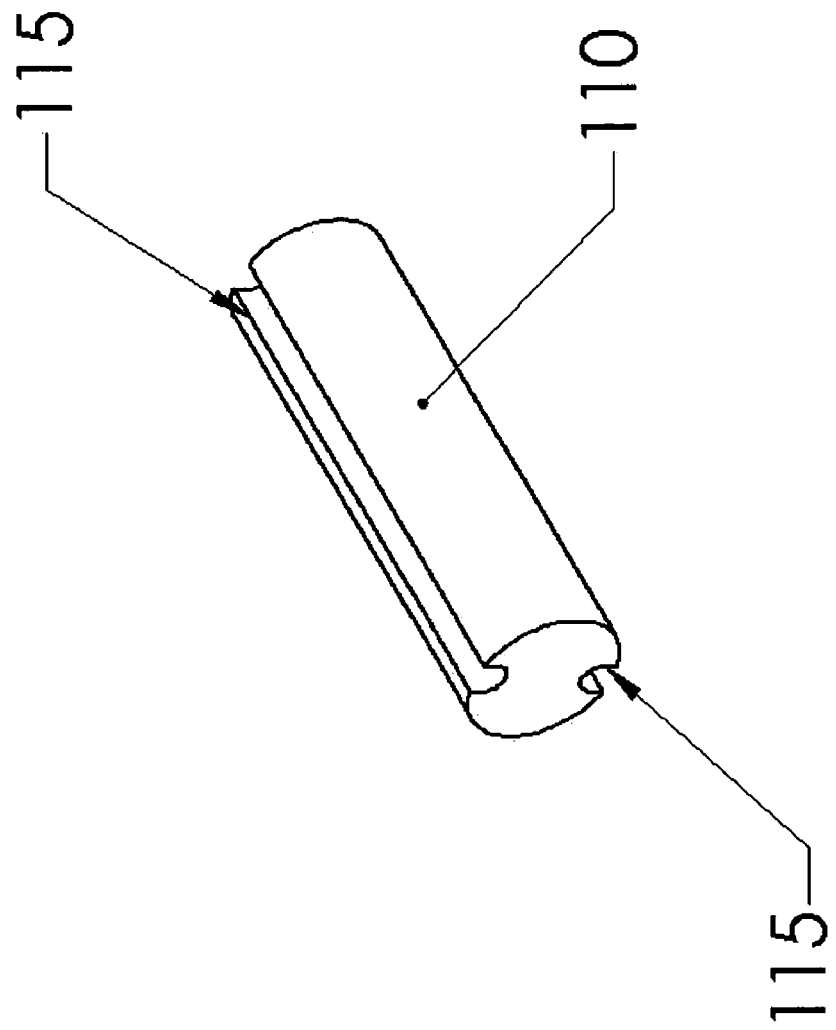
FIG. 10 is a detail isometric view of an exemplary retainer.

FIG. 10 is a detail isometric view of an exemplary retainer 110, showing the grooves 115 that run the length of the retainer.

Figure 11:
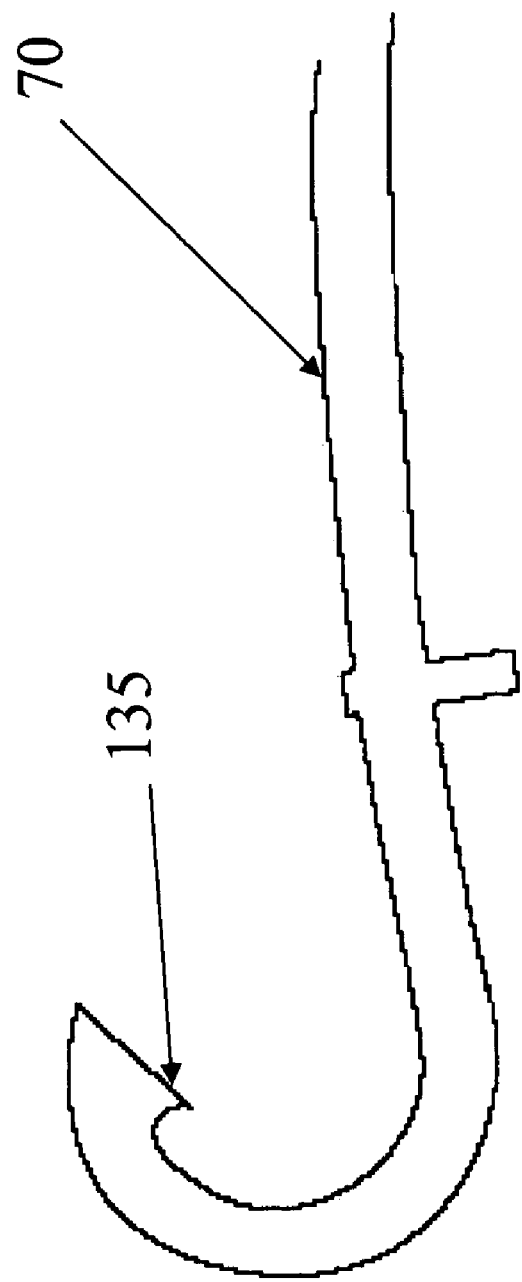
FIG. 11 is a detail view of an exemplary hook with a barb.

FIG. 11 is an exemplary leg 70 with a hook and a barbed anchoring member 135. The barbed anchoring member 135, in this embodiment, as shown, is positioned at the end of a hook at the distal end of a leg 70. A barbed anchoring member 135 may be included to improve the security of tissue or other material engagement. For example, once engaged with material, it is possible that a leg 70 may disengage when such disengagement is not directed or intended. With a barbed anchoring member 135, however, it may be less likely for the leg 70 to become disengaged because the barbed anchoring member 135 may serve to further hold the tissue or other material.

The devices of the present invention specifically may be used in a broad variety of applications where endoscopic joining of body tissue or other material is appropriate, for example suturing, stapling, or tissue or other material apposition. When used within a body, the devices of the present invention may be used, for instance, to join an unwanted separation of soft tissue that results from, for example and without limitation, injury, disease, or surgical incision. The devices and methods of the present invention also may be used in joining, or for example grafting, healthy tissue or other material onto areas of defective tissue or other material. Also, the devices and methods of the present invention may be used to approximate and/or fixate tissue or other material within a body. Further, the devices may be used to join, for example traversing and/or anchoring, one or more layers of tissue that can be accessed endoscopically, such as, for example and without limitation, the wall of a hollow or solid organ, duct, vessel or soft tissue structure.

The device of the present invention may offer various advantages over known devices. For instance, the independent nature of the legs 70 may allow them to be deployed and engaged without interfering with each other, and may also allow the legs to reach across a greater span of tissue or other material and therefore close larger tears or defects than previously possible. The independent nature of the legs 70 also may allow for better positioning during endoscopic procedures. Finally, the various leg 70 configurations may allow a surgeon to choose the configuration that may address and hold a given tear or defect more securely.

In use, the device of the present invention may be fed through the working channel of an endoscope. Once the device is deployed through the endoscope, it may be positioned near a tear or other defect. Positioning around a tear or defect may be improved by rotating the inner tube 20 to align the legs 70 in accordance with the orientation of the tear or defect by a control in the hand piece. Once positioning is complete, a leg 70 may be advanced and maneuvered through manipulation of its control cable 50 and guide block 60 so as to engage tissue or other material on one side of the tear or defect. For instance, if a hook configuration is used, the tissue or other material may be hooked by the first leg. A second leg 70 may then be advanced and maneuvered through its control cable 50 and guide block 60 to engage a different piece of tissue or other material surrounding the tear or defect. The amount of extension of the second leg relative to the extension of the first leg may be adjustable. This feature of the devices of the present invention allows the device to address tears or defects of various sizes, shapes and orientations. Additional legs 70 may continue to be advanced as needed to address the tear or defect. While use of the present invention generally is described in terms of extending and engaging the legs 70 of the device sequentially, it also is contemplated that the legs 70 may be (i) advanced simultaneously and engaged with the tissue or other material sequentially, (ii) advanced sequentially and engaged simultaneously or (iii) advanced and engaged simultaneously.

Once a sufficient number of legs have been advanced and engaged with the tissue or other material surrounding the tear or defect, the quality of engagement between each leg and the tissue or other material may be tested by applying a light tension to each leg by pulling each control cable 50. Once satisfied with the anchoring of the legs within the tissue or other material, the pusher tube assembly 10 (inner tube 20 and end cap 30) may push the clamp collar 100 forward until the clamp collar 100 contacts the tabs 120 on the legs 70. The advancement of the clamp collar 100 may draw the deployed legs 70 back together into a closed and locked position, thus drawing the various segments of tissue or other material surrounding a tear or other defect into apposition. If necessary, the clamp collar 100 also may be undeployed. For instance, if one or more of the deployed legs is not positioned sufficiently or has become dislodged or disengaged from the tissuse or other material, the collar 100 may be undeployed and the leg or legs may be repositioned and/or reengaged with the tissue or other material.

Once advancement of the clamp collar 100 has pulled the legs 70 into a closed and locked position, thus leading to a closure of a tear or defect or apposition of tissue or other material, the legs 70 may be broken to free the actuated clip from the endoscopic device. The legs 70 may be broken at the weakened zones 80 of the curved areas 90 by applying an increasing load to the control cables 50 until a sudden loss of tension is detected. Because the hook tab 120, in the activated position, abuts the pusher tube assembly 10, all forces placed on the legs 70 during breaking should be absorbed into the device and no significant forces should be transmitted to the tissue or other material surrounding the clip. After separation from the endoscopic device, the endoscope may be removed while the clip may be left in place. In this manner, the devices of the present invention may effectively lead to the closure of tears or other defects and apposition of tissue or other material, analogous to that caused by conventional suturing or stapling.

The embodiments of the present invention may be configured and controlled by a proximal handle that may control the extension and retraction of the independent legs 70 as well as rotate and extend and retract the inner tube 20 independently of the outer tube 40. In one embodiment of the present invention, the proximal handle of the device may be connected or connectable to the inlet port of the endoscope or echo-endoscope. Examples of such endoscopes are found, for example, in U.S. Pat. No. 6,638,213; No. 6,614,595; and No. 6,520,908. In another embodiment, the proximal handle of the device of the present invention may be screwed and thereby securely anchored into the inlet port of the instrumentation channel of the endoscope using a Luer lock mechanism.

The control cables 50 of the present invention may be housed within the inner tube 20 of the present invention. These control cables 50 may independently control the extension and retraction of the legs 70 of the present invention. In one embodiment of the present invention, the control cables 50 may be flexible in bending. In another embodiment, the control cables 50 may be metal cables. In another embodiment, the control cables 50 of the present invention may be solid stainless steel wire. In another embodiment the control cables 50 may have a diameter of about 0.50 mm. Further, in one embodiment of the present invention, the control cables 50 may travel to the proximal handle through the approximate center of the inner tube 20. In another embodiment, the control cables 50 may travel to the proximal handle towards the outer circumference of the inner tube 20. The control cables 50 may be connected or connectable to the proximal handle.

The outer tube 40 of the present invention may serve several functions. It may protect the instrumentation channel in the endoscope from the device of the present invention, as well as to protect the device itself. The outer tube 40 may reinforce the device and also may help to guide and position the device appropriately, even after the device has moved beyond the passage provided in the endoscope. The outer tube 40 also may serve to dilate or enlarge a tissue penetration tract. In one embodiment of the present invention, the outer tube 40 may be separate from the rest of the device of the present invention. Thus, in this embodiment, the outer tube 40 may be moved independently of the rest of the device. In another embodiment of the present invention, the outer tube 40 be made of an impenetrable material. In another embodiment of the present invention, the outer tube may be a flexible plastic tube. In another embodiment of the present invention, the outside diameter of the outer tube 40 may be of an appropriate size to allow for easy insertion into the working channel of most endoscopes. In another embodiment of the present invention, the outside diameter of the outer tube 40 may be about 2.5 mm. In another embodiment, the inside diameter of the outer tube 40 may be about 2.0 mm. The outer tube 40 may be connected or connectable to the proximal handle.

The pusher tube assembly 10 of the present invention may comprise an inner tube 20 that may reside within the outer tube 40, as well as an end cap 30 that may be fitted and secured to the distal end of the inner tube 20. This pusher tube assembly 10 may be similar to those used in many endoscopic accessories. In one embodiment of the present invention, the pusher tube assembly 10 may be flexible, but also may be able to support axial compressive loads when restrained in the outer tube 40. In another embodiment of the present invention, the inner tube 20 may consist of a coiled stainless steel tube. In another embodiment of the present invention, the pusher tube assembly 10 may have an outside diameter of about 1.65 mm. In another embodiment of the present invention, the pusher tube assembly 10 may have an inside diameter of about 1.52 mm. The inner tube 20 of the pusher tube assembly 10 may be connected or connectable to the proximal handle.

Ligating clips generally are classified according to their geometric configuration as either symmetric or asymmetric clips. Symmetric clips are generally "U" or "V" shaped clips that are substantially symmetrical about a central, longitudinal axis extending between the legs of the clip. By contrast, asymmetric clips lack an axis of symmetry. Because the legs 70 of the clips of the present invention are not joined at their proximal ends, the clips of the present invention can be symmetrical or asymmetrical in use. This feature of the legs 70 of the present invention allows the clips to address tears or other defects of various shapes, sizes and orientations.

When the legs 70 of the present invention include a barbed anchoring member 135, in one embodiment, the barbed anchoring member 135 may include a pointed conical tip. In another embodiment, the barbed anchoring member 135 may pierce one or more layers of tissue or other material in a pre-expansion form before expanding into an anchoring shape.

The clips of the present invention can be made of any material using conventional fabrication methods. For instance, materials that may be used in accordance with the present invention may include conventional biocompatible materials such as various metals, plastics, elastomers, and bioabsorbable polymeric materials, as well as stainless steel, and other surgical alloys of steel. In general it may be valuable to avoid using materials that are likely to cause allergic reactions or inflammation, unless such a result is desired. Examples of bioabsorbable polymeric materials that may be used in accordance with the present invention include, for example and without limitation, homopolymers and copolymers of glycolide, lactide and para-dioxanone, trimethylene carbonate and epsilon-caprolactone. When made of a biooabsorbable polymeric material, the clips of the present invention may be made by injecting a suitable polymer melt into an appropriately designed mold at process conditions conventionally employed for such polymer systems. After the polymer melt cools, the molded polymer shaped in the mold to meet the design criteria of the clip may be released from the mold. The molded clip can then be sterilized using conventional methods to render the clip suitable for surgical applications. In one embodiment of the present invention, the clips may be made of a spring hardened stainless steel such as, for example, 17-7 PH in the CH900 condition (hardened). In another embodiment of the present invention, the clip may be formed of wire with a diameter of about 0.25 mm prior to hardening.

In various embodiments of the present invention, the legs 70 of the clips may have weakened zones 80 to allow the clips to separate from the endoscopic device once positioned and drawn into a locked position. In one embodiment of the present invention, the weakened zone 80 may be created by reducing the diameter of the leg wire. In another embodiment, the weakened zone may be designed to fail when a tension load of about one pound is applied to the legs 70 through the control cables 50 and actuating members 60.

Other embodiments and advantages of the present invention will be apparent to those skilled in the art from consideration of the specification and the practice of the invention disclosed herein. It is intended that the specification and examples be considered as exemplary only.

What is claimed is:

1. A device comprising:
   an outer tube with a proximal end and a distal end;
   a pusher tube assembly comprising an inner tube with a proximal end and a distal end and an end cap secured to said distal end of said inner tube;
   a clamp collar within said distal end of said inner tube;
   legs, each having a proximal end and a distal end;
   a retainer located proximally to said clamp collar with slots that allow passage of said legs; and
   actuating members connected to said proximal end of said legs;
   wherein each of said legs has an outwardly-oriented tab;
   wherein said distal ends of said legs are located, before deployment, at said distal end of said inner tube but proximal to said clamp collar;
   wherein said legs, said actuating members and said retainer reside within said inner tube; and
   wherein said outer tube and said inner tube are connected to a proximal handle that may actuate each leg independently through a separate control cable connected to the proximal end of each of said actuating members of said legs.

2. The device of claim 1, wherein said distal end of said legs comprises a hook having a back end.

3. The device of claim 2, wherein said back end of said hook is angled outwardly within said inner tube.

4. The device of claim 1, wherein said legs comprise a barbed anchoring member.

5. The device of claim 1, wherein said actuating members comprise guide blocks.

6. The device of claim 1, wherein said proximal handle rotates said inner tube independently of said outer tube.

7. The device of claim 1, wherein said inner tube comprises a coiled stainless steel tube.

8. The device of claim 1, wherein said clamp collar further comprises slots to allow passage of said legs.

9. The device of claim 1, wherein said inner tube, said legs, and said actuating members are controlled by said proximal handle to interlock said legs.

10. The device of claim 9, wherein said interlocked legs are releasable.

11. The device of claim 9, wherein said legs comprise a weakened portion that can break and separate said legs from said device once said legs are extended from said device and in a closed and locked position.

12. The device of claim 1, comprising two or more legs.

13. The device of claim 1, comprising three or more legs.

14. The device of claim 1, comprising four or more legs.

15. The device of claim 1, wherein said legs comprise a sharpened end.

16. The device of claim 15, wherein said sharpened end is protected when said legs have been extended from said device and are in a closed and locked position.

17. The device of claim 1, wherein said legs comprise a spring material.

18. The device of claim 1, wherein said outer tube comprises a coil toward its distal end.

19. The device of claim 1, wherein said inner tube comprises a coil toward its distal end.

20. A method of endoscopically joining material using the device of claim 1, wherein said joining comprises:
   extending a first leg from said inner tube;
   engaging a target material with said distal end of said first leg;
   extending a second leg from said inner tube;
   engaging target material with said distal end of said second leg;
   drawing said legs together into an interlocked position; and
   releasing said legs in said interlocked position from said device.

21. The method of claim 20, further comprising repeating said extending and said engaging with additional legs as needed.

22. The method of claim 20, wherein said extending is accomplished by sliding said actuating members connected to said proximal ends of said legs.

23. The method of claim 20, wherein said engaging is accomplished by hooking said target material.

24. The method of claim 20, wherein said engaging is accomplished by anchoring said target material.

25. The method of claim 20, wherein said drawing is accomplished by sliding said inner tube over said extended and engaged legs.

26. The method of claim 20, wherein said legs are extended and engaged sequentially.

27. The method of claim 20, wherein said legs are extended and engaged simultaneously.

28. The method of claim 20, wherein said target material comprises tissue.

29. The method of claim 20, wherein said target material surrounds a tear.

30. The method of claim 20, wherein said target material comprises tissue on alternate sides of a tear.

31. The method of claim 20, wherein said method is used to repair a tissue defect.

32. The method of claim 20, wherein said releasing step comprises applying a force to said legs through said actuating members that may break said legs at a weakened portion of said legs.

* * * * *